US012602148B2

(12) United States Patent
Kale et al.

(10) Patent No.: US 12,602,148 B2
(45) Date of Patent: Apr. 14, 2026

(54) SYSTEM AND METHOD FOR DIAGNOSIS AND ANALYSIS OF MEDICAL IMAGES

(71) Applicant: PathForce Technologies, Inc., Irvine, CA (US)

(72) Inventors: Mohit A. Kale, Mission Viejo, CA (US); Michael F. Colaco, Newport Beach, CA (US)

(73) Assignee: PathForce Technologies, Inc., Irvine, CA (US)

( * ) Notice: Subject to any disclaimer, the term of this patent is extended or adjusted under 35 U.S.C. 154(b) by 64 days.

(21) Appl. No.: 18/455,680

(22) Filed: Aug. 25, 2023

(65) Prior Publication Data

US 2024/0077997 A1 Mar. 7, 2024

Related U.S. Application Data

(60) Provisional application No. 63/404,287, filed on Sep. 7, 2022.

(51) Int. Cl.
| | |
|---|---|
| *G06F 3/04845* | (2022.01) |
| *G06F 3/01* | (2006.01) |
| *G06F 3/0485* | (2022.01) |
| *G06F 3/16* | (2006.01) |
| *G06T 7/00* | (2017.01) |
| *G16H 30/20* | (2018.01) |
| *G16H 30/40* | (2018.01) |
| *G16H 50/20* | (2018.01) |
| *H04L 9/40* | (2022.01) |
| *G06F 3/0482* | (2013.01) |

(52) U.S. Cl.
CPC .......... *G06F 3/04845* (2013.01); *G06F 3/012* (2013.01); *G06F 3/017* (2013.01); *G06F 3/0485* (2013.01); *G06F 3/167* (2013.01); *G06T 7/0012* (2013.01); *G16H 30/20* (2018.01); *G16H 30/40* (2018.01); *G16H 50/20* (2018.01); *H04L 63/0815* (2013.01); *H04L 63/0861* (2013.01); *G06F 3/0482* (2013.01); *G06F 2203/04806* (2013.01); *G06T 2200/24* (2013.01); *G06T 2207/20092* (2013.01)

(58) Field of Classification Search
CPC .................................................. G06F 3/04845
See application file for complete search history.

(56) References Cited

U.S. PATENT DOCUMENTS

| | | | |
|---|---|---|---|
| 10,572,996 B2 | 2/2020 | Euren | |
| 2014/0334696 A1 | 11/2014 | Gholap | |
| 2018/0197624 A1* | 7/2018 | Robaina et al. | ....... G16H 10/60 |

(Continued)

*Primary Examiner* — James J Debrow
(74) *Attorney, Agent, or Firm* — Renner, Otto, Boisselle & Sklar LLP

(57) ABSTRACT

The present invention provides a method and system for the diagnosis and analysis of medical images. More specifically, the system of the present invention focuses on the usage of wearable devices in the field of Pathology and around creating a workflow for the pathologists that helps them analyse, diagnose, and sign off a case using digital technology and wearable devices. The system of the present invention comprises a wearable device, a cloud-based computing platform, data storage, a plurality of interaction modules, and a processing module. The wearable device extends the field of vision by creating a more immersive experience for better diagnosis of the pathological case.

27 Claims, 6 Drawing Sheets

(56)              References Cited

U.S. PATENT DOCUMENTS

2021/0257084  A1*   8/2021  Freeman et al. ....... G16H 30/40
2021/0330416  A1*  10/2021  Redmond et al. ..... A61B 90/36
2022/0354440  A1*  11/2022  Grajales .............. A61B 5/7465
2022/0366680  A1*  11/2022  Rasolzadeh et al. .. G06V 10/80
2023/0196562  A1*   6/2023  Sue et al. ............. G06T 7/0012

* cited by examiner

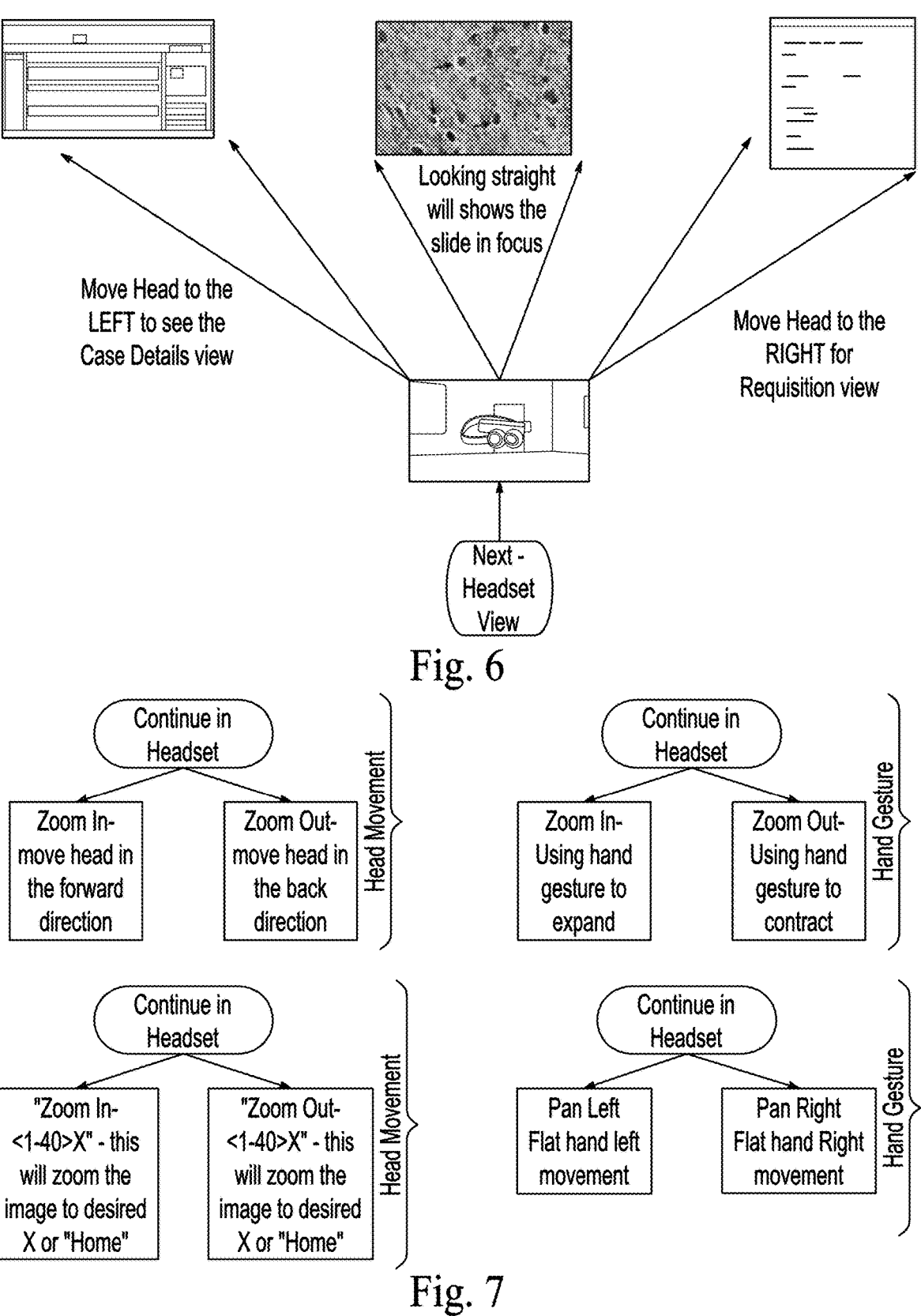

Looking straight
will shows the
slide in focus

Move Head to the
LEFT to see the
Case Details view

Move Head to the
RIGHT for
Requisition view

Next -
Headset
View

Fig. 6

Continue in
Headset

Zoom In-
move head in
the forward
direction

Zoom Out-
move head in
the back
direction

Head Movement

Continue in
Headset

Zoom In-
Using hand
gesture to
expand

Zoom Out-
Using hand
gesture to
contract

Hand Gesture

Continue in
Headset

"Zoom In-
<1-40>X" - this
will zoom the
image to desired
X or "Home"

"Zoom Out-
<1-40>X" - this
will zoom the
image to desired
X or "Home"

Head Movement

Continue in
Headset

Pan Left
Flat hand left
movement

Pan Right
Flat hand Right
movement

Hand Gesture

Fig. 7

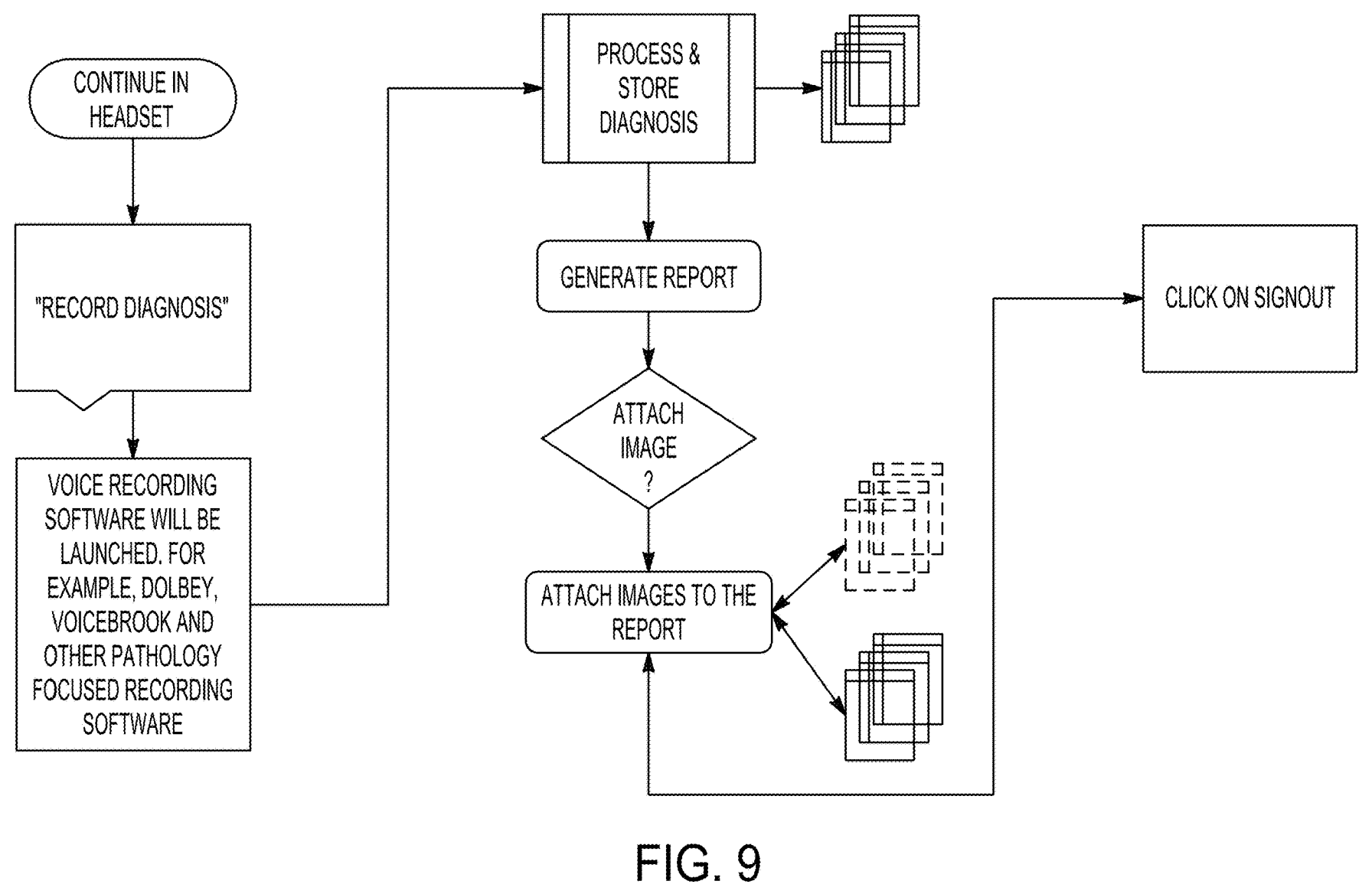

CLICK ON SIGNOUT

PROCESS & STORE DIAGNOSIS

GENERATE REPORT

ATTACH IMAGE ?

ATTACH IMAGES TO THE REPORT

CONTINUE IN HEADSET

"RECORD DIAGNOSIS"

VOICE RECORDING SOFTWARE WILL BE LAUNCHED. FOR EXAMPLE, DOLBEY, VOICEBROOK AND OTHER PATHOLOGY FOCUSED RECORDING SOFTWARE

FIG. 9

SYSTEM AND METHOD FOR DIAGNOSIS AND ANALYSIS OF MEDICAL IMAGES

BACKGROUND

A. Technical Field

The present disclosure relates to a method and system for digital pathology, more particularly the disclosure relates to a system and method for analysing and diagnosing medical images for digital pathology.

B. Background Art

In the present global scenario, Digital Pathology (DP) has been a fast-growing field over the last few years, especially with the advent of Covid where the Food and Drug Administration (FDA) in the United States and the European Medicines Agency (EMA) in the European Union have approved DP as an acceptable medium to perform diagnostics. Digital pathology includes the acquisition, management, sharing, and interpretation of pathology information including slides and data in a digital environment. To drive the efficiencies in DP, the digital experience for pathologists must be customized to extend their field of vision and create a more immersive experience to better diagnose.

U.S. Pat. No. 10,572,996 discloses a method for annotating a tissue slide image, a system and a method performed by a computing system for detecting pathological anomalies in a digital pathology image are disclosed. The method performed by a computing system for detecting pathological anomalies in a digital pathology image includes providing a digital pathology image to the computing system and analyzing the digital pathology image using an identification module arranged on the computing system. The identification module uses a machine learning module to execute recognizing an object containing an abnormal image pattern using an identification model loaded in said identification module and identifying whether the abnormal image pattern corresponds to a pathological anomaly using the identification model.

US Patent Application 20140334696 discloses a digital pathology imaging method may comprise receiving a plurality of image sections on a cloud server, the plurality of image sections being a result of splitting an initial digital image; stitching the plurality of image sections on the cloud server into a reconstituted digital image; and providing access to the reconstituted digital image. A system for digital pathology imaging may comprise a cloud server for receiving a plurality of image sections, wherein the cloud server comprises an image stitching module configured to stitch the plurality of image sections into a reconstituted digital image. Also, a system for digital pathology imaging may comprise: an image preprocessor configured to preprocess an initial digital image such that correct alignment of a plurality of tiles are enabled; an image splitter configured to split the initial digital images into a plurality of image sections with a stitching provision in pixels; and an asynchronous messaging module configured to push the plurality of image sections to the cloud server.

In addition, in DP, the use of a laptop or personal computer (PC) exists, which does not mimic the microscope. Further, the laptop or personal computer (PC) does not provide the field of vision that the microscope provides. The experience on a PC/laptop can potentially degrade a pathologist's field of vision due to distractions from the physical world.

Hence, there is a need in the art for a system and method thereof that entirely occupies the field of view of slides, and analyse, diagnose, and sign-offs a case using digital technology.

SUMMARY OF THE INVENTION

The present invention provides a method and system for the diagnosis and analysis of medical images. The system of the present invention focuses on the usage of wearable devices in the field of Pathology. More specifically, the system of the present invention focuses around creating a workflow for pathologists that helps them analyse, diagnose, and sign off a case using digital technology and wearable devices. The system of the present invention comprises a wearable device, a computing platform that is cloud based or on-premise, data storage, a plurality of interaction modules, and a processing module. Further, the system of the present invention is accompanied by controllers, and/or hand gestures, and/or voice-enabled commands to empower the pathologist with an end-to-end interaction from analysing, diagnosing, and closing a case.

The system of the present invention, a system for diagnosis and analysis of medical images is comprise of a wearable device, a computing platform, a data storage, a plurality of interaction modules, a processing module, a laboratory information system (LIS). The computing platform of the system of the present invention is embedded with Artificial Intelligence and configured to use Artificial Intelligence, cellular and wireless networks to view medical images, analyse them, and diagnose the pathological case. The wearable device headset of the system of the present invention is configured to communicatively connect and link it to the computing platform, virtually import images, virtually enable user to perform end-to-end interaction for standard operations of zoom in/out, pan, measure, compare multiple images side-by-side and annotate by tagging for research, tumor board, education or other needs that may be deemed useful by the Pathologists to view medical images, analyse them, and diagnose the pathological case. The data storage of the system of the present invention is integrated through a cloud image store and a cloud data store. The plurality of interaction modules of the system of the present invention are configured in synchronization with the wearable device to enable user/pathologist to interact with the computing platform using any one of the interaction modules or a combination thereof. The processing module of the system of the present invention is configured to provide custom build models that mimic the problem-solving and decision-making capabilities of the human mind to identify Regions of Interest (RoI) that will aid the quick analysis and diagnosis of the whole slide images. The laboratory information system (LIS) is configured to accession the case under analysis for diagnosing the pathological case.

The method of the present invention, a method for diagnosis and analysis of medical images comprising steps of digitizing slide by scanning and uploading the slide to a cloud image store and accessioning a case by the laboratory information system LIS. The method includes applying by computing platform in communication with processing module an AI model. The method includes detecting the arrival of new files. The method includes running the newly arrived file as soon as its arrival is detected through an Artificial intelligence based quality check. The method includes retaining the original format, e.g.WSI format or converting the file to a DICOM format using a conversion tool. The method includes referencing the image as soon as the conversion of the file is done for a case and making it ready to be rendered. The method includes wearing by the user a wearable device headset, synchronizing a plurality of interaction modules with the wearable device headset, and communicatively connecting and linking it to the computing platform. The method includes log-in by the user to the system with their credentials. The method includes presenting by computing platform the user at the wearable device headset with a user Dashboard as a landing page. The method includes selecting interaction mode for interacting with the computing platform by selecting and enabling one or more interaction module from the Dashboard. The method includes requesting by the user using selected interaction mode to navigate to the desired Case view list, the desired Case view list being an active case list including but not limited to in-process, pending, open, closed, new, on-hold, re-scan list and any other state that may be encoded as a part of the system implementation. The method includes opening by the computing platform at the wearable device headset the desired Case view list. The method includes opening by the user the desired case Accession ID details in Case details view. The method includes launching the viewer at the wearable device headset. The method includes performing by the user zoom in or zoom out for better view. The method includes performing by the user Pan—left or Pan—right for desired view. The method includes creating annotations by the user. The method includes sniping a portion of the view by the user. The method includes comparing multiple images side-by-side, measuring a desired tissue area and tagging for research, tumor board, education or other needs that may be deemed useful by the user/Pathologists. The method includes exiting out of the image control by the user by pronouncing 'Home' or pronouncing "Virtual Keyboard" and/or clicking on the ESC key. The method includes recording diagnostics and closing the case.

DETAILED DESCRIPTION OF THE DRAWINGS

The embodiments can be better understood with reference to the following drawings and description. The components in the figures are not necessarily to scale, the emphasis instead being placed upon illustrating the principles of the embodiments. Moreover, the figures, like reference numerals designate corresponding parts throughout the different views.

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

The above and other objects, features, and advantages of the present invention will be more clearly understood from the following detailed description taken in conjunction with the accompanying drawings, in which:

FIG. 6 illustrates a rendering visualization in the second stage of the method of the present invention according to one or more embodiments of the present invention.

FIG. 7 illustrates various methods of diagnosing the digitized medical image in the third stage of the method of the present invention according to one or more embodiments of the present invention.

FIG. 9 illustrates flow diagram of recording diagnosis, preparing reports, and closing case in the fourth stage of the method of the present invention according to one or more embodiments of the present invention.

Figure 1:
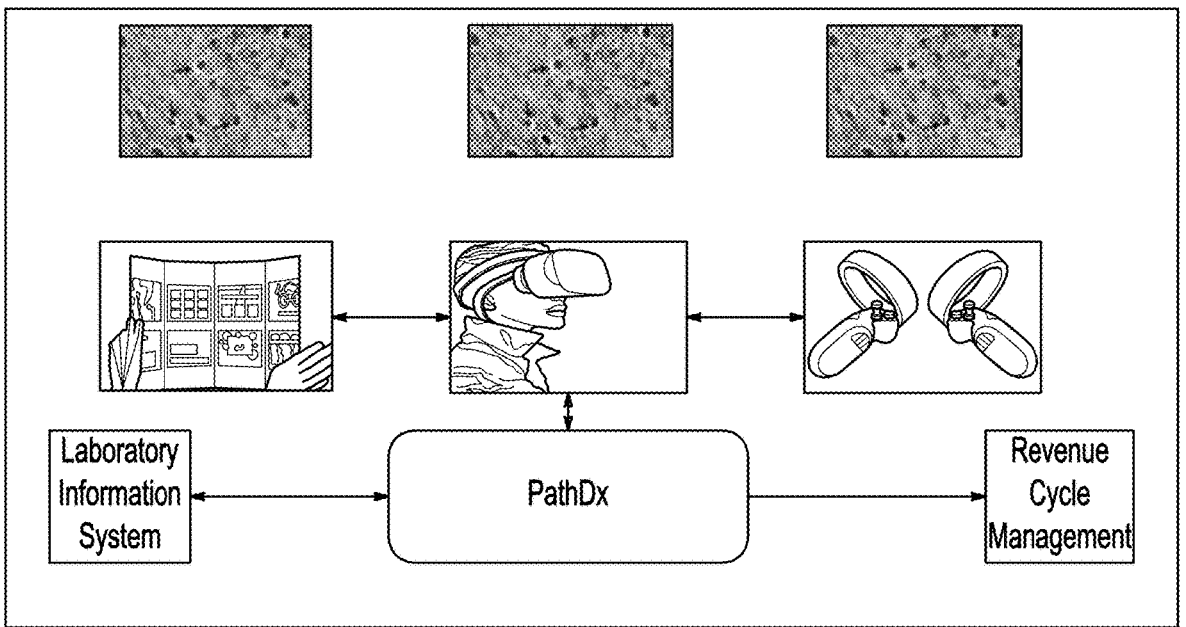
FIG. 1 illustrates a system block diagram of the system for diagnosis and analysis of medical images, according to an exemplary implementation of the present invention.

It should be appreciated by those skilled in the art that any block diagrams herein represent conceptual views of illustrative systems embodying the principles of the present invention. Similarly, it will be appreciated that any flow-charts, flow diagrams, and the like represent various processes which may be substantially represented in a computer-readable medium and so executed by a computer or processor, whether or not such computer or processor is explicitly shown.

DETAILED DESCRIPTION OF THE INVENTION

The embodiments herein provide a method and system for digital pathology, more particularly a system and method for providing optimized analysis and diagnosis of medical images in digital pathology. The method creates a workflow for the pathologists that helps them analyse, diagnose, and sign off a case using digital technology. Further, the embodiments may be easily implemented in communication and management structures. Embodiments may also be implemented as one or more applications performed by stand-alone or embedded systems.

The present invention can overcome the limitations of the prior art system by entirely occupying the field of vision, and providing end-to-end interaction from analyzing, diagnosing, and closing a case. The present invention provides a method for performing diagnosis and analysis of the medical images of any pathological slides in an efficient and accurate manner, providing end-to-end interaction-based controllers for the pathologist to study and analyse by manipulating the images in the system, and allowing to shuffle between various mediums of interaction, omnichannel rendering of images, and AI and NLP based diagnosis.

In the following description, for the purpose of explanation, specific details are set forth in order to provide an understanding of the present invention. It will be apparent, however, to one skilled in the art that the present invention may be practiced without these details. One skilled in the art will recognize that embodiments of the present invention, some of which are described below, may be incorporated into a number of systems.

Furthermore, connections between components and/or modules within the figures are not intended to be limited to direct connections. Rather, these components and modules may be modified, re-formatted, or otherwise changed by intermediary components and modules.

References in the present invention to "one embodiment" or "an embodiment" mean that a particular feature, structure, characteristic, or function described in connection with the embodiment is included in at least one embodiment of the invention. The appearances of the phrase "in one embodiment" in various places in the specification are not necessarily all referring to the same embodiment.

Hereinafter, embodiments will be described in detail. For clarity of the description, known constructions and functions will be omitted.

Parts of the description may be presented in terms of operations performed by at least one electrical/electronic circuit, a computer system, using terms such as data, state, link, fault, packet, and the like, consistent with the manner commonly employed by those skilled in the art to convey the substance of their work to others skilled in the art. As is well understood by those skilled in the art, these quantities take the form of data stored/transferred in the form of non-transitory, computer-readable electrical, magnetic, or optical signals capable of being stored, transferred, combined, and otherwise manipulated through mechanical and electrical components of the computer system and the term computer system includes general purpose as well as special purpose data processing machines, switches, and the like, that are standalone, adjunct or embedded. For instance, some embodiments may be implemented by a processing system that executes program instructions so as to cause the processing system to perform operations involved in one or more of the methods described herein. The program instructions may be computer-readable code, such as compiled or non-compiled program logic and/or machine code, stored in a data storage that takes the form of a non-transitory computer-readable medium, such as a magnetic, optical, and/or flash data storage medium. Moreover, such processing system and/or data storage may be implemented using a single computer system or may be distributed across multiple computer systems (e.g., servers) that are communicatively linked through a network to allow the computer systems to operate in a coordinated manner.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, steps may be performed by a combination of hardware, software, firmware, and/or by human operators.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to a computer program(s) coded in accordance with various methods described herein, and the method steps of the invention could be accomplished by modules, routines, subroutines, or subparts of a computer program product.

In some embodiments, the systems may be configured as a distributed system where one or more components of the system are distributed across one or more networks in a cloud computing system.

As used in the description herein, the meaning of "a, an," and "the" includes plural reference unless the context clearly dictates otherwise. Also, as used in the description herein, the meaning of "in" includes "in" and "on" unless the context clearly dictates otherwise.

Exemplary embodiments will now be described more fully hereinafter with reference to the accompanying drawings, in which exemplary embodiments are shown. This invention may, however, be embodied in many different forms and should not be construed as limited to the embodiments set forth herein. These embodiments are provided so that this invention will be thorough and complete and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

While embodiments of the present invention have been illustrated and described, it will be clear that the invention is not limited to these embodiments only. Numerous modifications, changes, variations, substitutions, and equivalents will be apparent to those skilled in the art, without departing from the spirit and scope of the invention.

In an implementation according to one of the embodiments, the present invention is a system and method thereof for the diagnosis and analysis of medical images. According to one of the embodiments, the system and method thereof of the present invention are directed to improve the Field of vision in digital pathology which is entirely occupied by the slide and to improve the pathologist's ability to work from anywhere where they have access to their personal/wearable devices. The medical images diagnosed and analysed by the system and method of the present invention includes but not limited to medical images of the Whole Slide Image (WSI) format and/or DICOM and/or any other format of the medical images.

FIG. 1 illustrates a top-level schematic diagram depicting the system diagnosing and analysing the medical images. The system comprises a wearable device, data storage, a cloud-based computing platform, a plurality of interaction modules, and a processing module.

In an implementation according to one of the embodiments, the data storage is integrated with the cloud image store and cloud data store. The cloud data store is further integrated with laboratory information systems (LIS), and revenue cycle management via the cloud scanning-based computing platform. Digital Pathology starts post the digitization of the slides gets completed. Once, the slides are scanned and uploaded to the cloud image store and a case has been accessioned by the laboratory information systems LIS, the wearable device enables importing of the 2D image, and then the pathologist can study and analyze it by manipulating it. The annotations can be performed which can be preserved at the same location.

In an implementation according to one of the embodiments, the wearable device is a Virtual Reality (VR) goggle(s). The cloud-based computing platform uses Artificial Intelligence, Cellular and Wireless networks, etc. to view medical images, analyse them, and diagnose the pathological case.

The plurality of interaction modules comprises a hand gesture module, a voice command module, and a controller module. The pathologist can interact with the cloud-based computing platform using any one of the interaction modules or a combination thereof. The hand gesture module allows the pathologist to interact with the wearable device using a plurality of human hand gestures tailored to the cloud-based computing platform. The cloud-based computing platform has pre-defined custom hand gestures to provide the pathologist the ability to zoom in/out, pan, and annotate/comment on the image. The pathologist can further combine hand gestures with voice commands or the controller module or both. The cloud-based computing platform provides a plurality of custom-defined voice commands to perform diagnostics, and end-to-end interaction for standard operations of zoom in/out, pan, and annotate. The pathologists can also create reports and close out a case using Voice commands. Further, the controller module includes handheld controllers.

In an implementation according to one of the embodiments, the pathologist uses voice commands in combination with hand gestures and a controller module. Further, the cloud-based computing platform along with the voice command module facilitates sharing and collaboration with other pathologist (s) in a remote location and/or within the same facility/office/vicinity/city/state using the VR headset and voice commands With the use of a combination of voice commands and gestures, the pathologist can communicate with their peers for a consult.

The system platform of the present invention is configured to use Artificial Intelligence (AI) and Natural Language Processing to bring personalized multiple mediums to analyse and diagnose their case. AI and Hyper Automation with integration to relevant backend system interfaces deliver better diagnostic experiences. The system and the method of the present invention are configured to provide custom build models that mimic the problem-solving and decision-making capabilities of the human mind to identify Regions of Interest (RoI) that will aid the quick analysis and diagnosis of the whole slide images. As the algorithm learns from reading more cases, the probability of accurately identifying ROIs increases.

In one of the implementations according to one of the embodiments, the system platform of the present invention and method thereof enables the clinician to identify the area(s) of malignant growth and identify the relevant area(s) to collect the tissue sample(s) from, in order for an accurate diagnosis by the pathologist. Further, as the AI model evolves, some of the cases can be simulated based on similarities in previous diagnoses.

Figure 2:
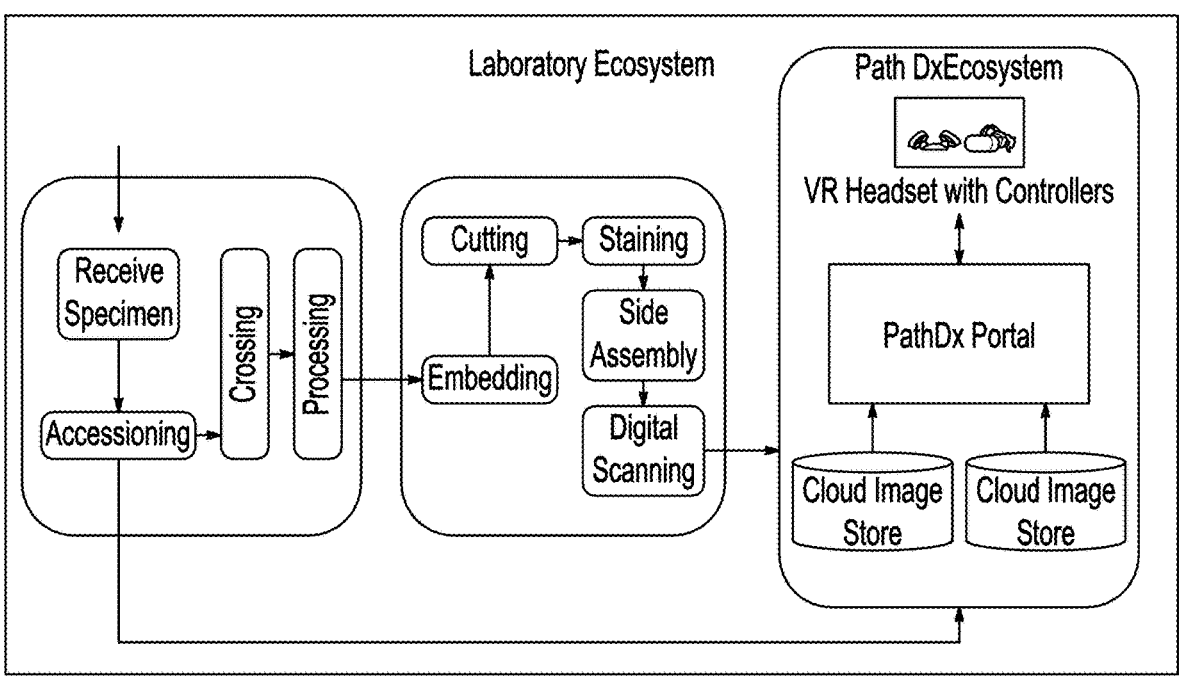
FIG. 2 illustrates a block diagram of the laboratory ecosystem including the system of the present invention, according to an exemplary implementation of the present invention.

FIG. 2 illustrates a block diagram of the laboratory ecosystem including the system of the present invention, according to an exemplary implementation of the present invention. As illustrated in the FIG. 2, when a case arrives in the laboratory, the specimen/sample goes through the readiness process of grossing, cutting, and being frozen on a glass slide. Post the digital scanning of the glass slide and before presenting it to the pathologist, the cloud-based computing platform with an AI model will be applied to each slide. The AI model reads the diagnosis requested, searched through its extensive database, and evaluates if there have been similar diagnoses that were provided. The proprietary algorithm will then match the incoming sample's request and create a fitment analysis. If the analysis returns an 85% match, the algorithm will continue to analyse and provide the pathologist with a side-by-side visual of the previous close sample and the current sample to continue their diagnosis. The model attributes will be defined to ensure the efficient processing of cases. Further, the digitized slide is presented to the computing platform of the system of the present invention for further diagnosing and analysing through the wearable device by the user/pathologist and generating the reports.

Figure 3:
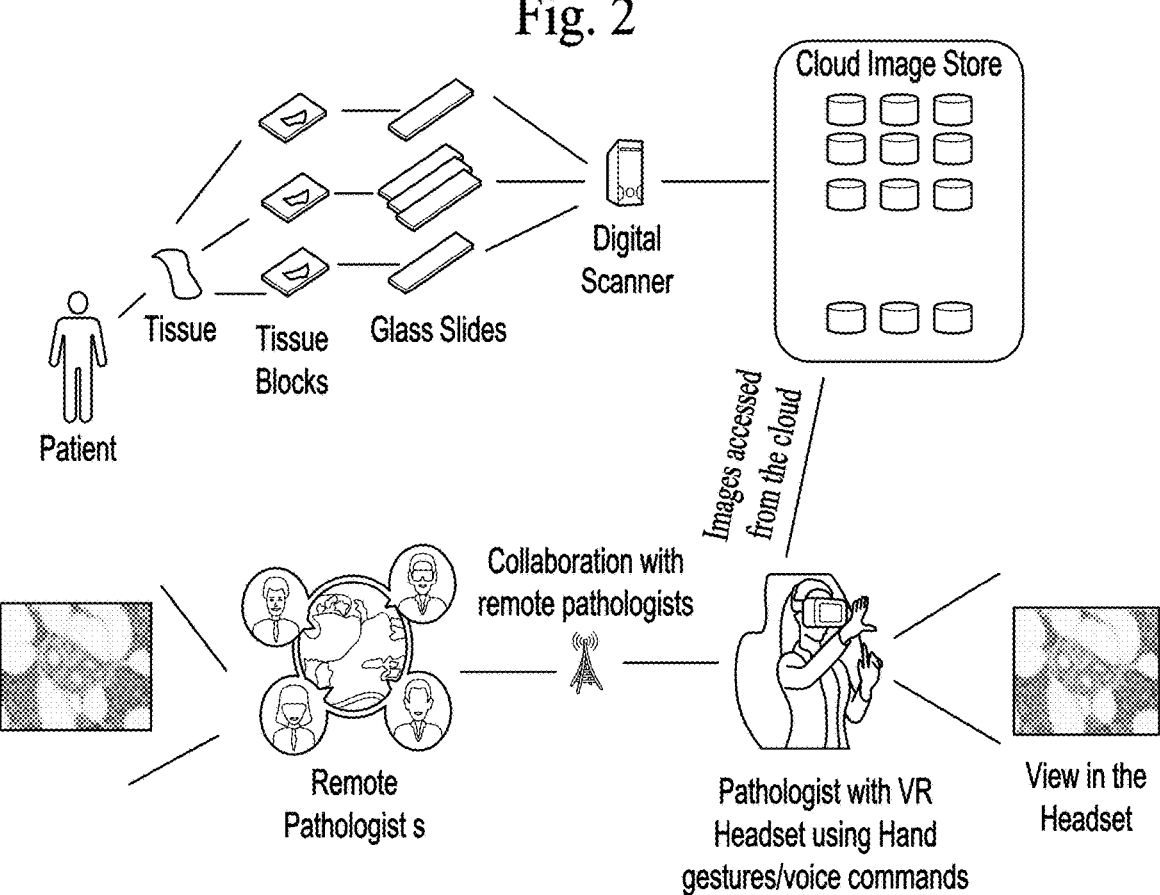
FIG. 3 illustrates a technical architecture executing a complete process flow of analysis, diagnosis, and collaboration for digital pathology according to one or more embodiments of the present invention.

FIG. 3 illustrates a technical architecture executing a complete process flow of analysis, diagnosis, and collaboration for digital pathology according to one or more embodiments of the present invention. As illustrated in the FIG. 3 the physical samples are digitized and are collected at a central repository or a storage system. The digitized samples are made available to the user/pathologists through networking systems controlled through the computing platform of the system of the present invention. The digitized samples are made available to the user/pathologists in virtual mode through wearable device headset that is a virtual reality visualization device configured to communicatively interact with the computing platform of the system enabling the user to perform necessary activities to analyse and diagnose the medical images and prepare a report.

Figures 4, 5:
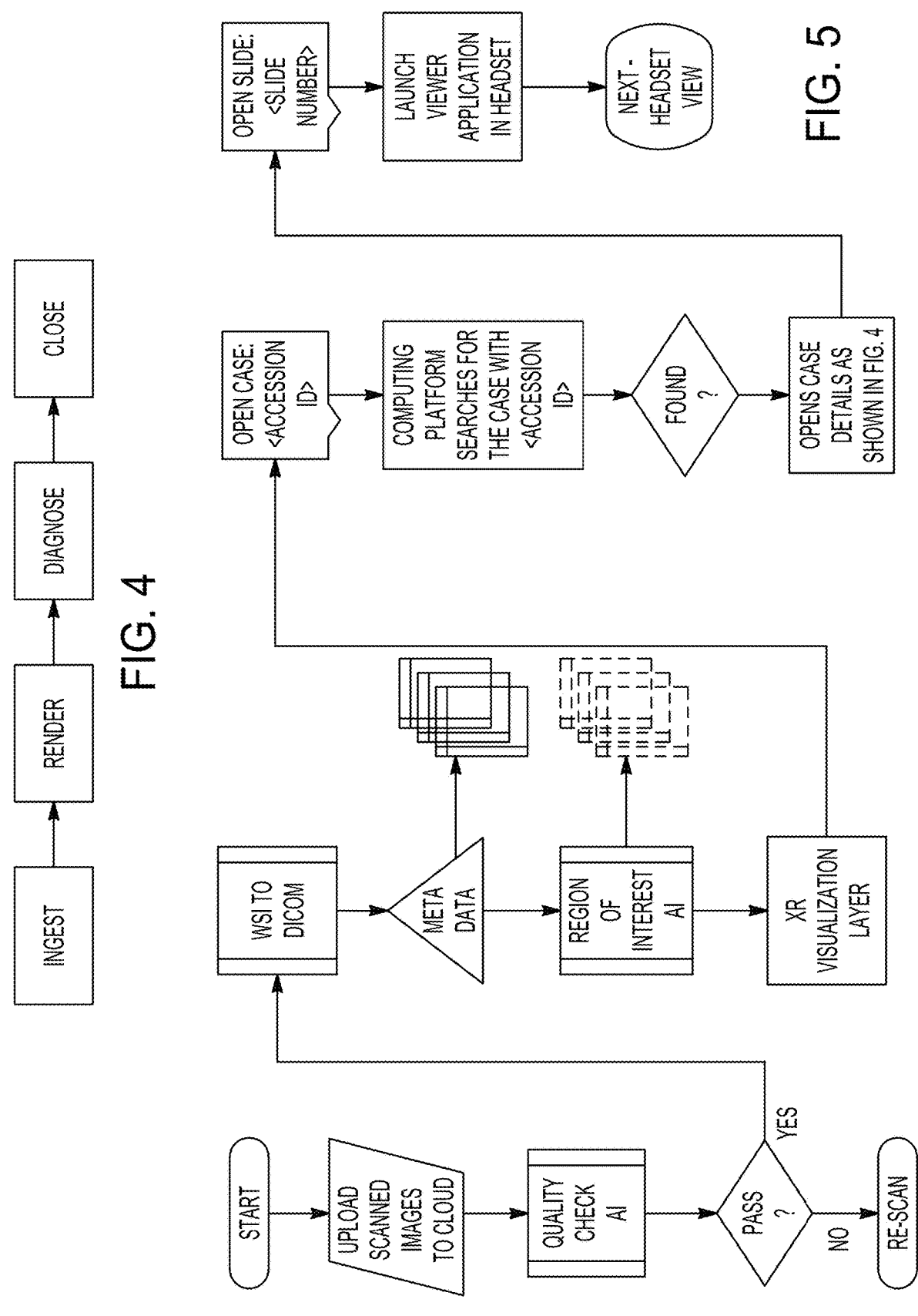
FIG. 4 illustrates a high level flow chart of the method of the present invention according to one or more embodiments of the present invention.
FIG. 5 illustrates a high level flow diagram of the first stage of the method of the present invention according to one or more embodiments of the present invention.

FIG. 4 illustrates a high level flow chart of the method of the present invention according to one or more embodiments of the present invention. As illustrated in the FIG. 4, in the first stage of the method the digitized medical image is ingested into the system along with requisition document for the analysis by the system. In the second stage of the method the ingested digitized medical image is rendered to the user for analysis and diagnosis through wearable device headset that is a virtual reality visualization device. In the third stage of the method the user analyses and diagnose the digitized medical image. In the fourth stage of the method the diagnosis is recorded, and reports are prepared, and the case is closed.

FIG. 5 illustrates a high level flow diagram of the first stage of the method of the present invention according to one or more embodiments of the present invention. As illustrated in the FIG. 5 the method includes step of digitizing slide by scanning and uploading the slide to a cloud image store. The method includes running the newly arrived file as soon as its arrival is detected through an Artificial intelligence based quality check. The method includes step of sending a re-scan request to the laboratory in the form of an email for the file that fails the quality control. The method includes retaining the original format, e.g.WSI format or converting the file to a DICOM format using a conversion tool upon successful quality check. The method step further includes extracting and storing metadata in Cloud SQL and accessing the stored data using BigQuery. The method includes step of identifying Regions of Interest (RoI) that will aid the quick analysis and diagnosis of the whole slide images. The method includes providing the dashboard as landing page of the visualization layer at the wearable device headset to the user. The method includes requesting by the user using selected interaction mode the desired case Accession ID. The method includes searching the desired case Accession ID details by the computing platform. The method includes opening by the user the desired case Accession ID details in Case details view. The method includes the step of selecting by the user the desired slide. The method includes launching the viewer at the wearable device headset.

FIG. 6 illustrates a rendering visualization in the second stage of the method of the present invention according to one or more embodiments of the present invention. As illustrated in the FIG. 6 the method includes step of rendering in the headset in the center visualization mode the selected image/ slide. The method further incudes step of showing the Case details in that window upon the user turning their head to left. Further, the method includes step of rendering the Requisition document upon the user turn their head to right.

FIG. 7 illustrates various methods of diagnosing the digitized medical image in the third stage of the method of the present invention according to one or more embodiments of the present invention. As illustrated in the FIG. 7 the method includes step of the method includes step of performing by the user zoom in or zoom out for better view. The step of performing zoom in/out by user includes step of user moving their head forward to zoom in to the desired zoom level, upto 40x, the user moving head back to zoom out to the desired zoom level. The step also includes the user providing voice command Zoom-In <1-40x> to zoom in to the desired zoom level, the user providing voice command Zoom out <40x-1x> to zoom out to the desired zoom level. The method further includes step of the user making 'Push' hand gesture to zoom into the desired zoom level, the user making 'Pull back' hand gesture to zoom out to the desired zoom level. The method includes step of performing by the user Pan—left or Pan—right for desired view. The step of performing Pan—left or Pan—right by the user includes steps of user performing hand gesture of flat hand movement to the left for pan left, user performing hand gesture of flat hand movement to the right for pan right.

Figure 8:
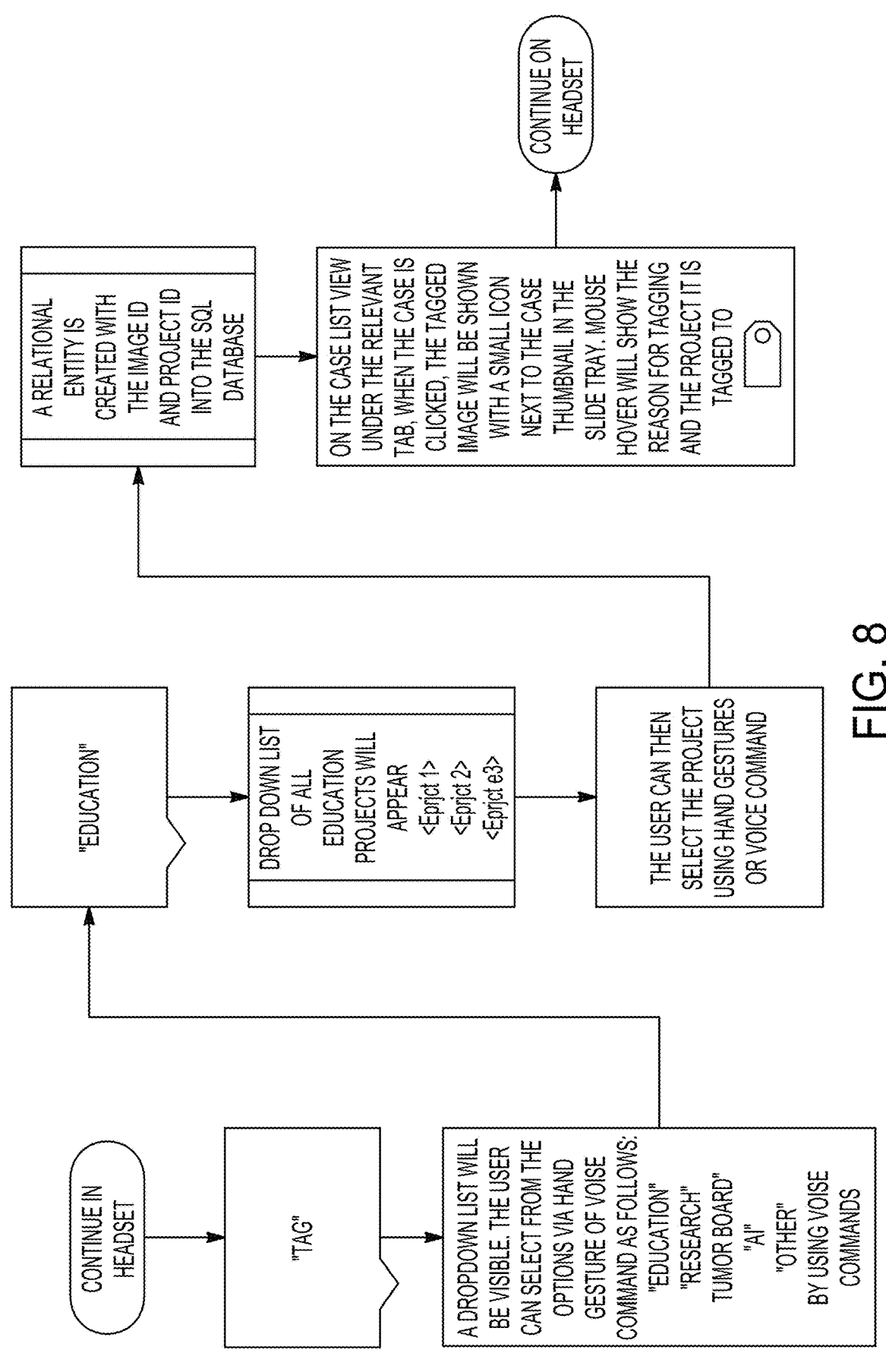
FIG. 8 illustrates flow diagram of Tagging a desired case for further use deemed appropriate by the Pathologist/user in the fourth stage of the method of the present invention according to one or more embodiments of the present invention.

FIG. 8 illustrates flow diagram of Tagging a desired case for further use deemed appropriate by the Pathologist/user in the fourth stage of the method of the present invention according to one or more embodiments of the present invention. As illustrated in the FIG. 8 the method includes step of providing by the user a command "TAG". The method step includes providing as a visual list, a dropdown list of tag category including but not limited to "EDUCA-TION", "RESEARCH", "TUMOR BOARD", "AI", and "OTHER". The method includes step of selecting by the user/pathologist desired tagging category from the option via hand gesture or voice command, presently for this example selecting "EDUCATION" by providing voice command. The method includes step of providing visually, upon receipt of command "EDUCATION", a dropdown list of all education projects to the user/pathologist. The method includes step of selecting by the user/pathologist the desired project from the dropdown list of all education projects using hand gestures or voice command. The method includes step of creating a relational entity with the image ID and selected project ID in to the SQL database. The method includes step of showing the tagged image with a small icon next to the case thumbnail in the slide tray on the Case List view under the relevant tab, when the case is clicked/ selected. The method step includes showing upon mouse hover the reason for tagging and the project it is tagged to.

FIG. 9 illustrates flow diagram of recording diagnosis, preparing reports, and closing case in the fourth stage of the method of the present invention according to one or more embodiments of the present invention. As illustrated in the FIG. 9 the method includes step of providing by the user a command "Record Diagnostics". The method includes step of processing and storing diagnosis generating report and attaching images to the report upon receiving the command "Record Diagnostics" from the user. The method further includes step of providing by the user a command "Close", to make the case ready to be signed out. The method includes further step of prompting a pop-up window to confirm that the user has indeed requested to Close/Sign-off the case and sign-off the case upon confirmation from the user.

Finally, the system enables the pathologist to sign-off cases and generate reports using Natural Language Process-ing-based AI algorithm. The pathologists can create the reports with a combination of gestures, voice commands, and controller(s) if so desired or using either of the features in their function.

According to one of the embodiments of the present invention a method for diagnosis and analysis of medical images comprising steps of digitizing slide by scanning and uploading the slide to a cloud image store and accessioning a case by the laboratory information system LIS. The method includes applying by computing platform in com-munication with processing module an AI model. The method includes detecting the arrival of new files. The method includes running the newly arrived file as soon as its arrival is detected through an Artificial intelligence based quality check. The method includes retaining the original format, e.g. WSI format or converting the file to DICOM format using a conversion tool. The method includes refer-encing the image as soon as the conversion of the file is done for a case and making it ready to be rendered. The method includes wearing by the user a wearable device headset, synchronizing a plurality of interaction modules with the wearable device headset, and communicatively connecting and linking it to the computing platform. The method includes log-in by the user to the system with their creden-tials. The method includes presenting by computing plat-form the user at the wearable device headset with a user Dashboard as a landing page. The method includes selecting interaction mode for interacting with the computing plat-form by selecting and enabling one or more interaction module from the Dashboard. The method includes request-ing by the user using selected interaction mode to navigate to open desired Case view list, the desired Case view list being an active case list including but not limited to in-process, pending, open, closed, new, on-hold, re-scan list and any other state that may be encoded as a part of the system implementation. The method includes opening by the computing platform at the wearable device headset the desired Case view List. The method includes opening by the user the desired case Accession ID details in Case details view. The method includes launching the viewer at the wearable device headset. The method includes performing by the user zoom in or zoom out for better view. The method includes performing by the user Pan—left or Pan—right for desired view. The method includes creating annotations by the user. The method includes sniping a portion of the view by the user. The method includes comparing multiple images side-by-side, measuring a desired tissue area and tagging for research, tumor board, education or other needs that may be deemed useful by the user/Pathologists. The method includes exiting out of the image control by the user by pronouncing 'Home' or pronouncing "Virtual Keyboard" and clicking on the ESC key. The method includes recording diagnostics and closing the case.

According to one of the embodiments the method of the present invention includes providing the user with the capa-bility of Tagging the desired case for research, education, tumor board or any other use deemed appropriate by the Pathologist using the command 'TAG' that will open a drop down list for user to select either of the options as follows 'EDUCATION', 'RESEARCH', 'TUMOR BOARD', 'AI', 'OTHER'. As an example, show in in FIG. 8 selecting 'EDUCATION' option will prompt open a dialog box that will highlight all the active Education projects. This will let the user select one or many of the listed projects. Once the image is tagged a small tag (icon) will appear next to the image on the slide tray. A mouse over the tag icon will show, why the image was tagged and the project ID(s) for which it was tagged In an implementation according to one of the embodiments of the present invention a method for diagnosis and analysis of medical images includes step of digitization of slide by scanning and uploading the slide to a cloud image store and accessioning a case by the laboratory information system LIS. The step of digitization of slide wherein the hi-resolution scanner scans the glass slide and stores it to a cloud image store in a computing platform's on-premise server storage environment or stores it directly to a cloud image store in computing platform's cloud storage environment.

In an implementation according to one of the embodiments of the present invention the method includes step of applying by computing platform in communication with processing module an AI model. The step of applying AI model includes step of reading diagnosis requested, searching through computing platforms extensive database at the data storage to evaluate if there have been similar diagnoses that were provided. The step further includes matching the incoming sample's request and creating a fitment analysis, and continuing to analyse and provide the pathologist with a side-by-side visual of the previous close sample and the current sample to continue their diagnosis if the analysis returns an 85% match.

In an implementation according to one of the embodiments of the present invention the method includes step of detecting arrival of new files. The step of detecting arrival of new files includes step of checking for arrival of new files by computing platform's cloud sync process by pinging an on-premise server at every predefined interval of time. The step of detecting arrival of new files includes step of receiving by computing platform's cloud sync process an alert from publish/subscribe API of arrival of new file(s) in the cloud storage environment. The predefined interval of time for pinging an on-premise server is configurable. The publish/subscribe API will alert the computation platform of arrival of new file(s) in the cloud storage environment.

In an implementation according to one of the embodiments of the present invention the method includes step of running the newly arrived file as soon as its arrival is detected through an Artificial intelligence based Quality Check. The step of running a file through an Artificial intelligence based Quality Check includes step of running a new file on its arrival through an Artificial intelligence based Quality Check. The step includes sending a re-scan request to the laboratory in the form of an email for the file that fails the quality control. Further, the step includes storing the original file or RAW file as-is upon passing the quality control, creating a copy file of the original file or RAW file that is stored.

In an implementation according to one of the embodiments of the present invention the method includes step of retaining the original format, e.g. WSI format or converting the file to DICOM format using a conversion tool. The step of converting the copy file to DICOM format using a conversion tool includes step of converting the original file or RAW file in the Whole Slide Image (WSI) format to DICOM format using a conversion tool embedded at the computing platform. The step further includes extracting and storing metadata in Cloud SQL and accessing the stored data using BigQuery and convert the DCM file to de-identified for research and AI/ML consumption. The method includes step of referencing the image as soon as the conversion of the file is done for a case and making it ready to be rendered.

In an implementation according to one of the embodiments of the present invention the method includes step of wearing by the user a wearable device headset, synchronizing a plurality of interaction modules with the wearable device headset, and communicatively connecting and linking it to the computing platform.

In an implementation according to one of the embodiments of the present invention the method includes step of user log-in to the system with their credentials. The step of user log-in to the system with their credentials includes step of user log-in to the system with their credentials using Single-Sign On feature. The step of user log-in to the system includes step of user log-in to the system with a retinal scan in the event user has signed-out. The method includes step of presenting by computing platform the user at the wearable device headset with a user Dashboard as a landing page.

In an implementation according to one of the embodiments of the present invention the method includes step of selecting interaction mode for interacting with the computing platform by selecting and enabling one or more interaction module from the Dashboard. The step of selecting interaction mode for interacting with the computing platform includes step of selecting and enabling a voice command module and a controller module for using Voice Commands (VC) for interacting with the computing platform. The step of selecting interaction mode for interacting with the computing platform includes step of selecting and enabling a hand gesture module and a controller module for using Hand gestures for interacting with the computing platform. The step further includes selecting and enabling a voice command module, a hand gesture module, and a controller module for using Voice Commands (VC) and Hand gestures both for interacting with the computing platform.

In an implementation according to one of the embodiments of the present invention the method includes step of requesting by the user using selected interaction mode to navigate to open desired Case view list. The step of requesting by the user to navigate to open desired Case view list includes step of requesting by the user using voice commands to navigate to open desired Case view list. The step further includes step of requesting by the user to navigate to desired Case view list by using hand gesture to select the "desired Case" view.

In an implementation according to one of the embodiments of the present invention the method includes step of opening by the computing platform at the wearable device headset the desired Case view List. The method includes step of opening by the user the desired case Accession ID details in Case details view. The step of opening by the user the desired case Accession ID details includes step of user providing voice command "Open <Accesion ID>" to navigate to the selected/desired case. The step also includes user using hand gestures to select the desired Accession ID.

In an implementation according to one of the embodiments of the present invention the method includes step of launching the viewer at the wearable device headset. The step of launching the viewer at the wearable device headset includes step of selecting by the user the desired slide. The step includes rendering in the headset in the center visualization mode the selected image/slide. The step further incudes showing the Case details in that window upon the user turning their head to left. Further, the step includes rendering the Requisition document upon the user turn their head to right. The step of selecting by the user the desired slide includes step of user providing voice command "Open Slide <ID>", user using hand gesture to select desired slide.

In an implementation according to one of the embodiments of the present invention the method includes step of performing by the user zoom in or zoom out for better view. The step of performing zoom in/out by user includes step of user moving their head forward to zoom in to the desired zoom level, upto 40×, the user moving head back to zoom out to the desired zoom level. The step also includes the user providing voice command Zoom-In <1-40×> to zoom in to the desired zoom level, the user providing voice command Zoom out <40×-1×> to zoom out to the desired zoom level. The method further includes step of the user making 'Push' hand gesture to zoom into the desired zoom level, the user making 'Pull back' hand gesture to zoom out to the desired zoom level.

The method includes step of performing by the user Pan—left or Pan—right for desired view. The step of performing Pan—left or Pan—right by the user includes steps of user performing hand gesture of flat hand movement to the left for pan left, user performing hand gesture of flat hand movement to the right for pan right.

In an implementation according to one of the embodiments of the present invention the method includes step of creating annotations by the user. The step of creating annotations by the user includes step of clicking by the user on an annotation icon. The step includes annotating over the desired area with selected annotation icon with two fingers (index and thumb) once the annotation icon is selected. The step further includes popping up comment/text box for the user to comment. Further, the step includes popping-up virtual keyboard for the user to use it to write comment. The step includes dictating by the user a desired comment by pressing the spacebar and holding the spacebar of virtual keyboard, typing by the user a desired comment using the virtual keyboard.

In an implementation according to one of the embodiments of the present invention the method includes step of sniping a portion of the view by the user. The step of sniping includes steps of clicking by the user on a Snip tool icon. The step includes selecting the desired area with selected Snip tool icon with two fingers (index and thumb) once the Snip tool icon is selected. Further, the step includes prompting a pop-up window to the user to save the snip in the desired location.

In an implementation according to one of the embodiments of the present invention the method includes step of measuring a desired tissue area. The step of measuring a desired tissue area includes step of clicking by the user on a Scale/Measure icon to select the icon and measuring a desired tissue area with selected Scale/Measure icon using a single finger once Scale/Measure icon is selected.

In an implementation according to one of the embodiments of the present invention the method includes step of tagging a desired case for further use deemed appropriate by the Pathologist/user. The method step of tagging a desired case for further use includes step of providing by the user a command "TAG". The method step includes providing as a visual list, a dropdown list of tag category including but not limited to "EDUCATION", "RESEARCH", "TUMOR BOARD", "AI", and "OTHER". The method includes step of selecting by the user/pathologist desired tagging category from the option via hand gesture or voice command, presently for this example selecting "EDUCATION" by providing voice command. The method includes step of providing visually, upon receipt of command "EDUCATION", a drop-down list of all education projects to the user/pathologist. The method includes step of selecting by the user/pathologist the desired project from the dropdown list of all education projects using hand gestures or voice command. The method includes step of creating a relational entity with the image ID and selected project ID into the SQL database. The method includes step of showing the tagged image with a small icon next to the case thumbnail in the slide tray on the Case List view under the relevant tab, when the case is clicked/selected. The method step includes showing upon mouse hover the reason for tagging and the project it is tagged to.

In an implementation according to one of the embodiments of the present invention the method includes step of exiting out of the image control by the user by pronouncing 'Home' or pronouncing "Virtual Keyboard" and clicking on the ESC key.

In an implementation according to one of the embodiments of the present invention the method includes step of recording diagnostics and closing the case. The step of recording diagnostics and closing the case includes steps of providing by the user a voice command "Record Diagnostics". The step includes processing and storing diagnosis generating report and attaching images to the report upon receiving the voice command "Record Diagnostics" from the user. Further, the step includes popping-up virtual keyboard for the user to use it to record their diagnosis. The step includes dictating by the user to record their diagnosis by pressing the spacebar and holding the spacebar of virtual keyboard. The step further includes providing by the user a voice command "Close", to make the case ready to be signed out. The step includes further step of prompting a pop-up window to confirm that the user has indeed requested to Close/Sign-off the case, sign-off the case upon confirmation from the user and rendering the Case Details Page for the user to select and use a similar workflow to diagnose the next case.

According to one of the embodiments of the present invention the system of the present invention, a system for diagnosis and analysis of medical images is comprise of a wearable device, a computing platform, a data storage, a plurality of interaction modules, a processing module, a laboratory information system (LIS). The computing platform of the system of the present invention is embedded with Artificial Intelligence and configured to use Artificial Intelligence, cellular and wireless networks to view medical images, analyse them, and diagnose the pathological case. The wearable device headset of the system of the present invention is configured to communicatively connect and link it to the computing platform, virtually import images, virtually enable user to perform end-to-end interaction for standard operations of zoom in/out, pan, and annotate to view medical images, analyse them, and diagnose the pathological case. The data storage of the system of the present invention is integrated through a cloud image store and a cloud data store. The plurality of interaction modules of the system of the present invention are configured in synchronization with the wearable device to enable user/pathologist to interact with the computing platform using any one of the interaction modules or a combination thereof. The processing module of the system of the present invention is configured to provide custom build models that mimic the problem-solving and decision-making capabilities of the human mind to identify Regions of Interest (RoI) that will aid the quick analysis and diagnosis of the whole slide images. The laboratory information system (LIS) is configured to accession the case under analysis for diagnosing the pathological case.

According to one of the embodiments the system of the present invention facilitates the user with the capability of Tagging the desired case for research, education, tumor board or any other use deemed appropriate by the Pathologist using the command 'TAG' that will open a dropdown list for user to select either of the options as follows 'EDUCATION', 'RESEARCH', 'TUMOR BOARD', 'OTHER'. The 'TUMOR BOARD' option will prompt open a dialog box that will highlight all the existing active Tumor Boards or the option to Create a new Tumor Board.

According to one of the embodiments of the present invention the plurality of interaction modules of the system of the present invention includes a hand gesture module, a voice command module, and a controller module. The hand gesture module is configured to allows the user/pathologist to interact with the wearable device headset using a plurality of human hand gestures tailored to the computing platform to perform diagnostics, and end-to-end interaction for standard operations of zoom in/out, pan, and annotate. The voice command module is configured to allows the user/pathologist to interact with the wearable device headset using a plurality of custom-defined voice commands to perform diagnostics, and end-to-end interaction for standard operations of zoom in/out, pan, and annotate. The controller module is configured to allows the user/pathologist to interact with the wearable device headset using a plurality of custom-defined control commands to perform diagnostics, and end-to-end interaction for standard operations of zoom in/out, pan, and annotate.

According to one of the embodiments of the present invention the computing platform of the system of the present invention is configured to receive a digitized slide at a cloud image store, apply in communication with processing module an AI model to the received digitized slide. The computing platform is configured to detect arrival of new files, run a new file through an Artificial intelligence based quality check, store the original file or RAW file as-is upon passing the quality control and create a copy file of the original file or RAW file that is stored. The computing platform converts the copy file to DICOM format using a conversion tool embedded at the computing platform and convert the DCM file to de-identified for research and AI/ML consumption. The computing platform facilitate the user login in interaction with the wearable device headset and a plurality of interaction modules. The computing platform provides the user desired Case view list in interaction with the wearable device headset and a plurality of interaction modules and further provides the user selected/desired case details, the desired slide in virtual viewer in interaction with the wearable device headset and a plurality of interaction modules. The computing platform processes and stores diagnosis, generate report and attach images to the report, and record diagnostics and close the case.

According to one of the embodiments of the present invention the wearable device headset of the system of the present invention presents virtually a Dashboard as a landing page to the user in interaction with computing platform. The wearable device headset enables the user to select interaction mode for interacting with the computing platform. The wearable device headset further enables the user to navigate to open desired Case view list, open the desired case Accession ID details in Case details view, launch the viewer, perform zoom in/out, Pan left/right for desired view, create annotations, snip a portion, measure a desired tissue area, record diagnostics, and close the case. The wearable device headset of the system of the present invention is configured to render in the headset in the center visualization mode the selected image/slide. The wearable device headset is configured to show the Case details in that window upon the user turning their head to left and render the Requisition document upon the user turn their head to right.

In an implementation according to one of the embodiments of the present invention the cloud data store is further integrated with laboratory information system (LIS), and revenue cycle management via the computing platform.

In an implementation according to one of the embodiments of the present invention the computing platform that is cloud based or on-premise.

In an implementation according to one of the embodiments of the present invention the wearable device headset is a Virtual Reality (VR) goggle(s).

The advantageous limitations of the system and method thereof includes:

Wearable device along with the Cloud-based and modular architecture enables a better field of vision entirely occupied by the side.

End-to-end interaction modules enable the pathologist to diagnose, analyse the medical image, and prepare a report based thereon.

Platform further allows collaborating with other pathologists to share and communicate for consult.

In some embodiments, the disclosed techniques can be implemented, at least in part, by computer program instructions encoded on a non-transitory computer-readable storage media in a machine-readable format, or on other non-transitory media or articles of manufacture. Such computing systems (and non-transitory computer-readable program instructions) can be configured according to at least some embodiments presented herein, including the processes shown and described in connection with Figures.

Further, while one or more operations have been described as being performed by or otherwise related to certain modules, devices, or entities, the operations may be performed by or otherwise related to any module, device, or entity.

Further, the operations need not be performed in the disclosed order, although in some examples, an order may be preferred. Also, not all functions need to be performed to achieve the desired advantages of the disclosed system and method, and therefore not all functions are required.

We claim:

1. A method for diagnosis and analysis of medical images, the method comprising steps of:

providing a wearable device headset, the wearable device headset comprising computing electronics that is configured to execute a plurality of interaction modules including at least a communications module and a display module;

executing the communications module with the computing electronics to access a laboratory information system with the wearable device headset;

executing the communications module with the computing electronics to obtain a digitized slide from an image store in the laboratory information system with the wearable device headset;

executing the display module with the computing electronics to display a plurality of views in a display of the wearable device headset, a first of the plurality of views comprising a display of the digitized slide and a second of the plurality of views comprising information pertaining to and separate from the digitized slide;

executing the communications module with the computing electronics to obtain one or more reference images with the wearable device headset from the image store in the laboratory information system;

utilizing the computing electronics to compare the digitized slide to the one or more reference images to render a diagnosis pertaining to the digitized slide based on the comparison; and executing the display module to render the diagnosis in the wearable device headset, and/or executing the communications module to transmit the diagnosis to a remote electronic device.

2. The method as claimed in claim 1 wherein the plurality of interaction modules further includes a user interface module that is configured to receive user commands to the wearable device headset for operation of the communication module and the display module.

3. The method as claimed in claim 2 wherein the interface module is configured to receive the user commands as at least one of voice commands, gesture commands, and head movements.

4. The method as claimed in claim 3, further comprising using a head movement user command to switch a view from among the plurality of views.

5. The method as claimed in claim 1, wherein the step of executing the communications module with the computing electronics to obtain the one or more reference images comprises:

reading a required diagnosis associated with the digitized slide from the laboratory information system;

searching the image store for images having a diagnosis relevant to the required diagnosis and identifying the one or more reference images as images having a diagnosis relevant to the required diagnosis; and receiving in the wearable device headset the identified one or more reference images.

6. The method as claimed in claim 1, wherein the plurality of views further includes a side-by-side view of the digitized image and at least one of the one or more reference images.

7. The method as claimed in claim 1, wherein the plurality of views further includes a centralized view that displays the digitized slide, a left side view that contains a first portion of the information pertaining to and separate from the digitized slide, and a right side view that contains a second portion of the information pertaining to and separate from the digitized slide.

8. The method as claimed in claim 7, wherein the centralized view, right side view, and left side view are displayed simultaneously.

9. The method as claimed in claim 7, wherein the centralized view, right side view, and left side view are displayed sequentially by selective operation of the computing electronics such that each of the plurality of views is rendered on an entire display of the wearable device headset.

10. A wearable device headset for diagnosis and analysis of medical images comprising:

a display module including a display for rendering images in the wearable device headset;

a communications module for electronic communication between the wearable device headset and an electronic device remote from the wearable device headset; and computing electronics that is configured to execute the communications module and the display module;

wherein the computing electronics is configured to:

execute the communications module to access a laboratory information system with the wearable device headset, execute the communications module to obtain a digitized slide from an image store in the laboratory information system with the wearable device headset;

execute the display module to display a plurality of views in the wearable device headset, a first of the plurality of views comprising a display of the digitized slide and a second of the plurality of views comprising information pertaining to and separate from the digitized slide;

execute the communications module with the computing electronics to obtain one or more reference images with the wearable device headset from the image store in the laboratory information system;

compare the digitized slide to the one or more reference images to render a diagnosis pertaining to the digitized slide based on the comparison; and execute the display module to render the diagnosis in the wearable device headset, and/or execute the communications module to transmit the diagnosis to a remote electronic device.

11. The wearable device headset as claimed in claim 10, wherein the computing electronics is configured to execute the communications module to obtain the one or more reference images by:

reading a required diagnosis associated with the digitized slide from the laboratory information system;

searching the image store for images having a diagnosis relevant to the required diagnosis and identifying the one or more reference images as images having a diagnosis relevant to the required diagnosis; and receiving in the wearable device headset the identified one or more reference images.

12. The wearable device headset as claimed in claim 10, further comprising a user interface module that is configured to receive user commands to the wearable device headset for operation of the communications module and the display module.

13. The wearable device headset as claimed in claim 12 wherein the user interface module is configured to receive the user commands as at least one of voice commands, gesture commands, and head movements.

14. The wearable device headset as claimed in claim 10, wherein the plurality of views further includes a centralized view that displays the digitized slide, a left side view that contains a first portion of the information pertaining to and separate from the digitized slide, and a right side view that contains a first portion of the information pertaining to and separate from the digitized slide.

15. The wearable device headset as claimed in claim 10 wherein the wearable device headset is an Augmented Reality or a Virtual Reality goggles.

16. A non-transitory computer readable medium for diagnosis and analysis of medical images that stores program code which when executed by an electronic processor performs the steps of:

executing a communications module in a wearable device headset to access a laboratory information system with the wearable device headset;

executing the communications module to obtain a digitized slide from an image store in the laboratory information system with the wearable device headset;

executing a display module in the wearable device headset to display a plurality of views in a display of the wearable device headset, a first of the plurality of views comprising a display of the digitized slide and a second of the plurality of views comprising information pertaining to and separate from the digitized slide;

executing the communications module to obtain one or more reference images with the wearable device headset from the image store in the laboratory information system;

comparing the digitized slide to the one or more reference images to render a diagnosis pertaining to the digitized slide based on the comparison; and executing the display module to render the diagnosis in the wearable device headset, and/or executing the communications module to transmit the diagnosis to a remote electronic device.

17. The non-transitory computer readable medium as claimed in claim 16, wherein executing the communications module with the computing electronics to obtain the one or more reference images comprises:

reading a required diagnosis associated with the digitized slide from the laboratory information system;

searching the image store for images having a diagnosis relevant to the required diagnosis and identifying the one or more reference images as images having a diagnosis relevant to the required diagnosis; and receiving in the wearable device headset the identified one or more reference images.

18. The non-transitory computer readable medium as claimed in claim 16, wherein the plurality of views further includes a side-by-side view of the digitized image and at least one of the one or more reference images.

19. The non-transitory computer readable medium as claimed in claim 16, wherein the plurality of views further includes a centralized view that displays the digitized slide, a left side view that contains a first portion of the information pertaining to and separate from the digitized slide, and a right side view that contains a second portion of the information pertaining to and separate from the digitized slide.

20. The non-transitory computer readable medium as claimed in claim 19, wherein the centralized view, right side view, and left side view are displayed simultaneously.

21. The non-transitory computer readable medium as claimed in claim 19, wherein the centralized view, right side view, and left side view are displayed sequentially by selective operation of the computing electronics such that each of the plurality of views is rendered on an entire display of the wearable device headset.

22. The non-transitory computer readable medium as claimed in claim 16, wherein the program code further is executed to implement a user interface module in the wearable device headset that is configured to receive user commands to the wearable device headset for operation of the communication module and the display module.

23. The non-transitory computer readable as claimed in claim 22 wherein the interface module is configured to receive the user commands as at least one of voice commands, gesture commands, and head movements.

24. The non-transitory computer readable as claimed in claim 23, further comprising using a head movement user command to switch a view from among the plurality of views.

25. A system for diagnosis and analysis of medical images, the system comprising:

a computing platform comprising a laboratory information system that includes an image store and a data store including information pertaining to and separate from the image store, and a wearable device headset for diagnosis and analysis of medical images, the wearable device headset comprising:

a display module including a display for rendering images in the wearable device headset;

a communications module for electronic communication between the wearable device headset and the computing platform remote from the wearable device headset; and computing electronics that is configured to execute the communications module and the display module;

wherein the computing electronics is configured to:

execute the communications module to access the laboratory information system with the wearable device headset;

execute the communications module to obtain a digitized slide from the image store in the laboratory information system with the wearable device headset;

execute the display module to display a plurality of views in the wearable device headset, a first of the plurality of views comprising a display of the digitized slide and a second of the plurality of views comprising information pertaining to and separate from the digitized slide;

execute the communications module with the computing electronics to obtain one or more reference images with the wearable device headset from the image store in the laboratory information system;

compare the digitized slide to the one or more reference images to render a diagnosis pertaining to the digitized slide based on the comparison; and execute the display module to render the diagnosis in the wearable device headset, and/or execute the communications module to transmit the diagnosis to the computing platform;

the wearable device headset being configured to communicatively connect with the computing platform using the communications module of the wearable device headset.

26. The system as claimed in claim 25, wherein the computing platform is cloud based.

27. The system as claimed in claim 25, wherein the wearable device headset is an Augmented reality or Virtual Reality goggles.

* * * * *